(12) United States Patent
Steppe et al.

(10) Patent No.: US 7,717,129 B2
(45) Date of Patent: May 18, 2010

(54) AUTOMATIC STOP COCK VALVE

(75) Inventors: Dennis L. Steppe, Riverside, CA (US); John C. Huculak, Mission Viejo, CA (US); Robert J. Sanchez, Jr., Oceanside, CA (US)

(73) Assignee: Alcon, Inc., Hunenberg (CH)

( * ) Notice: Subject to any disclaimer, the term of this patent is extended or adjusted under 35 U.S.C. 154(b) by 376 days.

(21) Appl. No.: 11/748,524

(22) Filed: May 15, 2007

(65) Prior Publication Data

US 2008/0066816 A1 Mar. 20, 2008

Related U.S. Application Data

(63) Continuation-in-part of application No. 11/522,648, filed on Sep. 18, 2006.

(51) Int. Cl.
*F16K 15/14* (2006.01)
*F16K 11/10* (2006.01)

(52) U.S. Cl. ............... 137/605; 137/607; 137/846; 604/90

(58) Field of Classification Search ............... 137/605, 137/607, 846; 604/90
See application file for complete search history.

(56) References Cited

U.S. PATENT DOCUMENTS

| | | | |
|---|---|---|---|
| 3,572,375 A | * | 3/1971 | Rosenberg ............... 137/512 |
| 3,706,355 A | | 12/1972 | Oglesbee |
| 4,063,555 A | * | 12/1977 | Ulinder ................ 604/247 |
| 4,535,818 A | * | 8/1985 | Duncan et al. ............ 137/846 |
| 4,612,960 A | * | 9/1986 | Edwards et al. ........... 137/846 |
| 5,285,808 A | | 2/1994 | Clanin |
| 5,449,051 A | | 9/1995 | Liao |
| 5,512,043 A | * | 4/1996 | Verkaart ................ 604/247 |
| 5,836,484 A | * | 11/1998 | Gerber ................. 222/494 |
| 2004/0102738 A1 | | 5/2004 | Dikeman et al. |
| 2006/0173420 A1 | | 8/2006 | Fangrow, Jr. |

FOREIGN PATENT DOCUMENTS

EP 0139347 A1 5/1985
EP 0340798 A1 11/1989

* cited by examiner

*Primary Examiner*—Stephen Hepperle
(74) *Attorney, Agent, or Firm*—W. David Lee

(57) ABSTRACT

A flow control device includes a fitting having three portals. One of the portals is an entry portal for a liquid, one of the portals is an entry portal for a gas, and the other portal is an exit portal for either the liquid or the gas. A normally closed back flow prevention valve is located in fitting. The back flow prevention valve prevents back flow of liquid through the fitting. The fitting and the backflow prevention valve also minimize or eliminate the formation of air bubbles in the liquid.

3 Claims, 2 Drawing Sheets

US 7,717,129 B2

AUTOMATIC STOP COCK VALVE

This application is a continuation-in-part of U.S. application Ser. No. 11/522,648 filed Sep. 18, 2006 entitled "Automatic Stop Cock Valve".

FIELD

The present invention pertains to a fluid flow fitting; more particularly the present invention pertains to a fluid flow fitting having a back flow prevention valve included therein.

BACKGROUND

In the process of performing medical procedures involving the use of different fluids, such as vitreoretinal surgery, it is not uncommon to use different gases and liquids. For example, in vitreoretinal surgery, the need may arise to exchange fluid from the interior of the eye and replace it with air.

In prior art vitreoretinal surgical systems, the exchange of fluid from the interior of the eye with air is typically performed by manually changing the position of a stop cock valve. The manual switching of the stop cock valve stops the flow of a primary fluid such as a surgical infusion solution (e.g. BSS PLUS® intraocular irrigating solution available from Alcon Laboratories, Inc. of Fort Worth, Tex.) and starts the flow of an alternate fluid such as air. When the time comes to stop the flow of surgical infusion solution and begin the flow of air, it has been necessary for the surgeon to verbally request that his assistant, fellow, scrub nurse or scrub tech in the operating room change the position of the stop cock valve. This technique can delay surgical procedures and lead to errors. If the stop cock valve is inadvertently turned to a non-functional position, the flow of fluid to the eye will be interrupted and the eye may go soft, thus further complicating an already delicate surgical procedure. Alternatively, improper manipulation of the stop cock valve introduces the possibility of unwanted back flow of the fluids.

Accordingly there remains a need in the art for a system and method that will provide a vitreoretinal surgeon direct control to shift between the flow of surgical infusion solution and the flow of air or other gas, without the potential for back flow, and without the need for assistance. Further, there remains a need in the art for a system and method that will eliminate the potential for the complication of a soft eye during surgery by a valve being turned to a non-functional position.

SUMMARY

There is provided by the disclosed invention a system and method which enables a vitreoretinal surgeon to switch between surgical infusion solution and air or other gas without the need for assistance and without creating the potential for a soft eye by having the flow of fluids interrupted.

In one aspect, the disclosed invention is a flow control system including a source for the flow of a first fluid, a source for the flow of a second fluid, means for switching between the flow of the first fluid and the flow of the second fluid, a first line for the flow of the first fluid, a second line for the flow of the second fluid; and a fitting. The fitting includes a first entry portal for the first line, a second entry portal for the second line, an exit portal for either the first fluid or the second fluid; a normally closed backflow prevention valve, and a receptacle. The backflow prevention valve is capable of being opened when the means for switching switches the flow of the first fluid to the flow of the second fluid. The receptacle has an internal surface closely mating with an external surface of the backflow prevention valve so as to minimize a gap volume between the receptacle and the external surface. Such a flow control system minimizes or eliminates the formation of air or gas bubbles in the first fluid, which is particularly advantageous in vitreoretinal or other medical applications.

BRIEF DESCRIPTION OF THE DRAWING FIGURES

A still better understanding of the automatic stop cock valve of the present invention may be had by reference to the drawing figures described below when read in conjunction with the Description of the Embodiments which follows, like numerals being used for like and corresponding parts of the various drawings.

DESCRIPTION OF THE EMBODIMENTS

While the disclosed invention is described herein according to its use with a vitreoretinal surgical system, those of ordinary skill in the understand will understand that the disclosed invention may be used with a variety of other equipment, both medical and non-medical, which require an operator to switch between flows of different fluids during an established procedure. In addition, while the disclosed invention is described herein in connection with switching a flow of liquid to a flow of gas and vice versa, it may also be used in connection with switching a flow of first liquid to a flow of a second liquid and vice versa.

Figure 1:
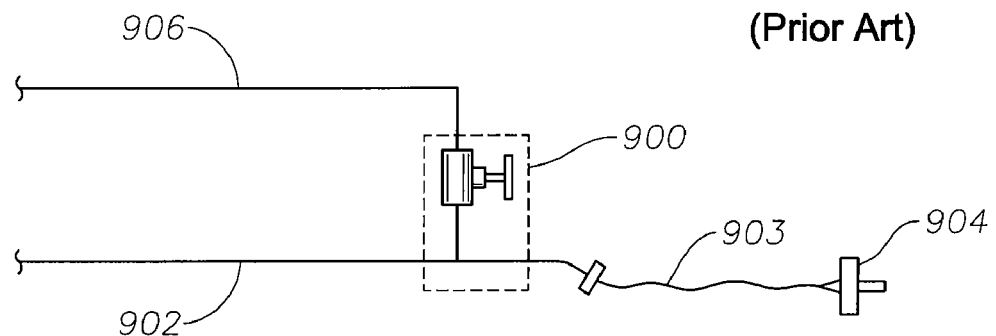
FIG. 1 is a schematic diagram of a prior art fluid flow system using a stop cock valve that is associated with a vitreoretinal surgical system.

As shown in FIG. 1, prior art fluid flow systems used by vitreoretinal surgeons typically include a manually actuated stop cock valve 900 for changing fluids supplied to a patient's eye through an infusion cannula 904 during surgery. During normal operation the infusion line 902 is open and air line 906 is closed, thus allowing a controlled flow of surgical infusion solution to the infusion cannula 904. When the need arises to switch from the flow of surgical infusion solution to air, the position of the stop cock valve 900 is manually changed. As previously indicated, if the stop cock valve 900 is inadvertently moved to a position which blocks the flow of both surgical infusion solution and air, the eye being operated on may go soft, thus adding further complications to what is already a delicate procedure.

According to the present invention, vitreoretinal surgeons will be provided with a new level of control of fluid flow during vitreoretinal surgery by being able to switch between fluids such as surgical infusion solution and air automatically. Such fluid flow from a source of surgical infusion solution or pressurized air may be changed by the use of an electrical switch on a footswitch or the input provided on a GUI (graphical user interface) control.

Figure 2:
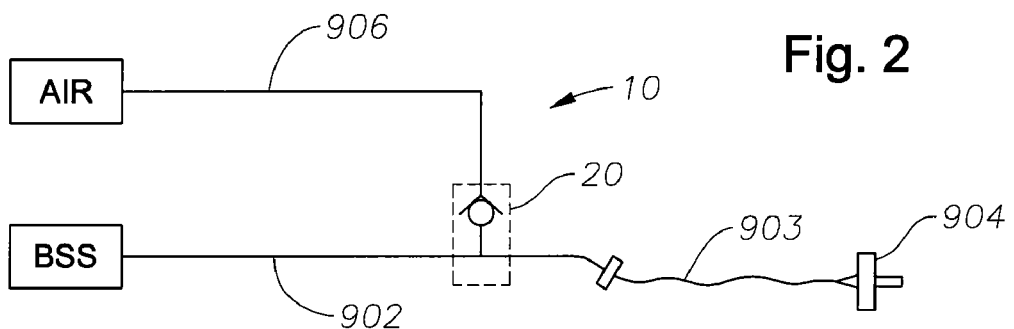
FIG. 2 is a schematic diagram of a fluid flow system using the automatic stop cock valve of the present invention.

As shown in FIG. 2, a system 10 incorporating the present invention replaces the prior art manually operated stop cock valve 900 with an automatic stop cock valve or a back flow prevention valve 20 which is constructed and arranged to enable the vitreoretinal surgeon to switch between fluids such as surgical infusion solution and air or other gas without the need to manually change the position of prior art stop cock valve 900. By removing the need to manually change the position of prior art stop cock valve 900, the surgeon's dependency on assistants, fellows, scrub nurses and/or scrub techs is reduced, and the potential problem of an interrupted flow by the switching of a prior art manually operated stop cock valve 900 to a non-functional position is avoided.

Figure 3:
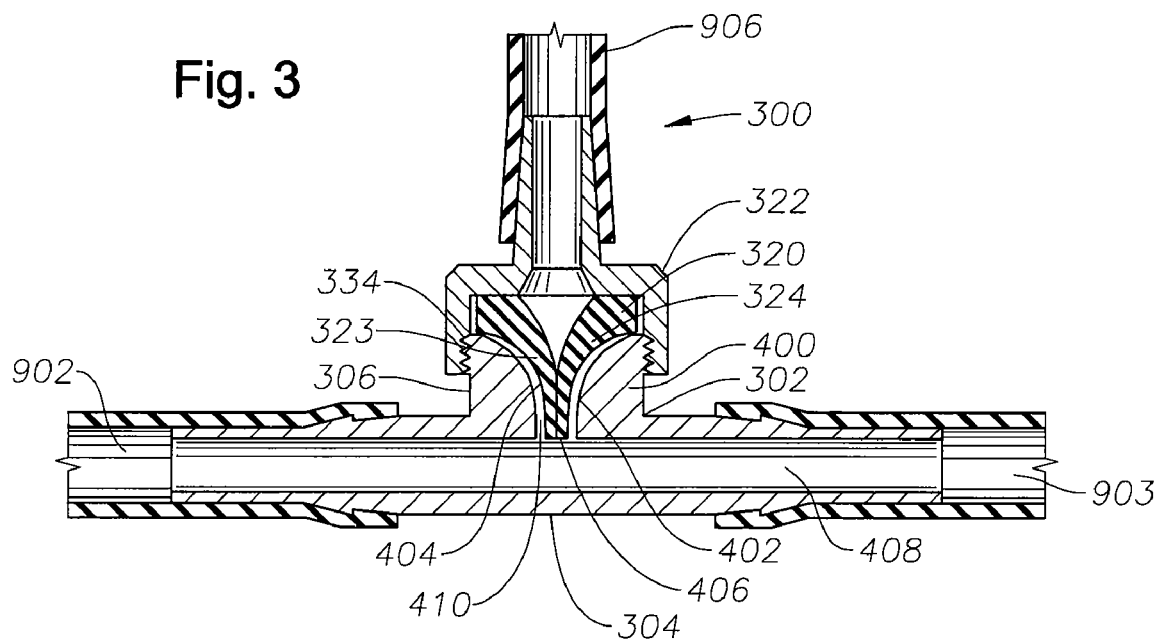
FIG. 3 is a side elevational view in partial section of a preferred embodiment of the automatic stop cock valve system of the present invention.

As may be seen in FIG. 3, the preferred embodiment 300 of the automatic stop cock valve 20 of the present invention is enclosed within a tee-shaped fitting 302. The tee-shaped fitting 302 is placed between the infusion line 902 and an air or gas line 906. When surgical infusion solution is flowing through the infusion line 902 to an infusion cannula 904, the surgical infusion solution flows through the straight portion 304 of the tee-shaped fitting 302. When the surgical infusion solution is de-activated and the source of air or gas is activated, the air flows through a stem portion 306 of the tee-shaped fitting 302 and opens a normally closed duck bill valve 320. The normally closed duck bill valve is held in place by a fitting 322 which is threadably 334 connected to the tee-shaped fitting 302. The two bill portions 323, 324 of the duck bill valve 320 will remain separated from one another as long as there is sufficient force from the flow of air through the stem portion 306 of the tee shaped fitting 302 to overcome the inherent bias in the beam strength of the two bill portions 323, 324 due to the elasticity of the rubber or flexible material from which the duck bill valve 320 is made. When the air pressure is no longer sufficient to keep the two bill portions 323, 324 separated from one another, the two bill portions 323, 324 will come together as shown in FIG. 3, thereby blocking the flow of fluid through the stem portion 306 of the fitting 302.

Accordingly, during normal infusion to the infusion cannula 904, as shown in FIG. 2, there is a controlled flow of surgical infusion solution. The air line 906 is closed. As shown in FIG. 3, the check valve 20, a duck bill valve 320 in the preferred embodiment 300, prevents any back flow of surgical infusion solution into the air line 906. When the vitreoretinal surgeon wants to switch from the infusion of surgical infusion solution to the infusion of air or other gas, the surgeon activates an electrical switch or touches a GUI. The surgical infusion solution pressure is decreased to a pressure less than the air or gas pressure and/or the air or gas pressure is increased to a pressure greater than the surgical infusion solution pressure. This causes the flow of surgical infusion solution through the infusion line 902 to terminate and the flow of air or gas through line 906 to begin. The pressure of the air or gas opens the check valve 20 thereby allowing air to be infused into the eye through a third line 903 connected to the infusion cannula 904. If desired, the switching of fluid can be reversed, thus allowing the vitreoretinal surgeon to switch from air or gas back to the infusion solution in the infusion line 902. In addition, manually, electrically, mechanically, or pneumatically actuated valves may also be disposed on infusion line 902 and air or gas line 906 to further enable the switching between infusion solution flow and air or gas flow. A preferred valve is a pinch valve.

Those of ordinary skill in the art will understand that while a duckbill valve 320 has been shown in the preferred embodiment 300, other types of back flow prevention valves may be used without departing from the present invention.

As shown in FIG. 3, stem portion 306 is formed with a receptacle 400 having an internal surface 402 closely mating with an external surface 404 of valve 320. In addition, a tip or opening surface 406 of valve 320 is disposed as close as possible to lumen 408 of straight portion 304 without placing valve 320 within the stream of fluid flow. Such a geometry of receptable 400 and disposition of valve 320 minimizes or eliminates the gap volume 410 between receptacle 400 and external surface 404, which in turn prevents the formation of air or gas bubbles within the infusion solution flow within portion 304. Prevention of such air or gas bubbles maximizes patient safety.

Figure 4:
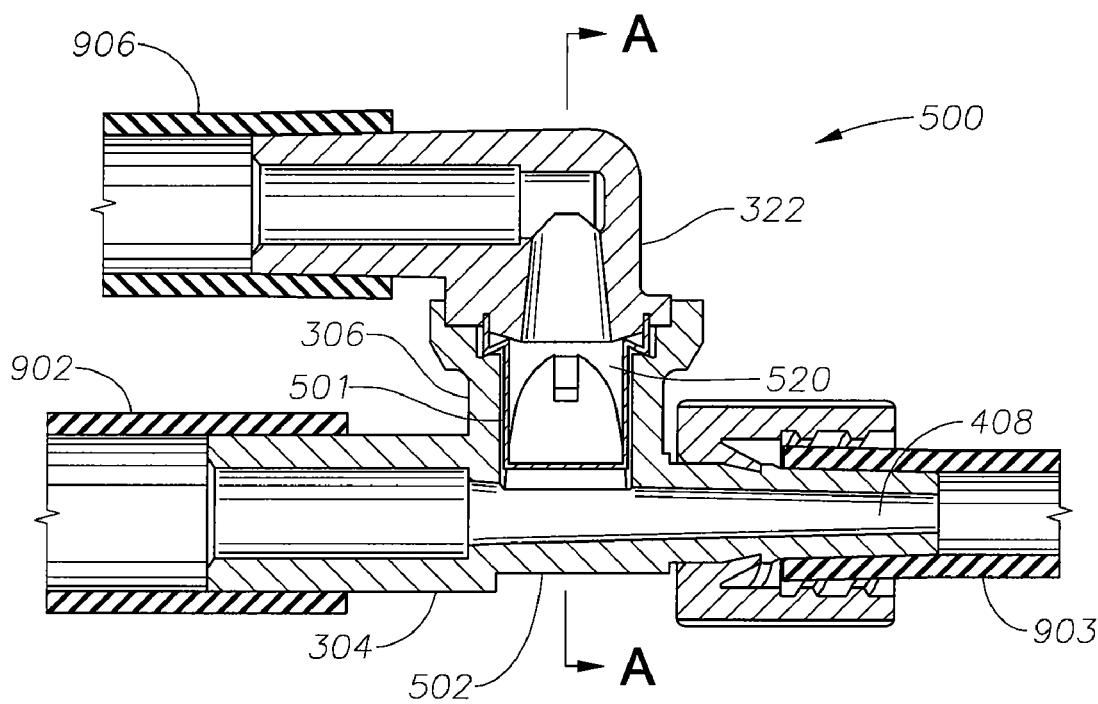
FIG. 4 is a side elevational view in partial section of a second, preferred embodiment of the automatic stop cock valve system of the present invention.
Figure 5:
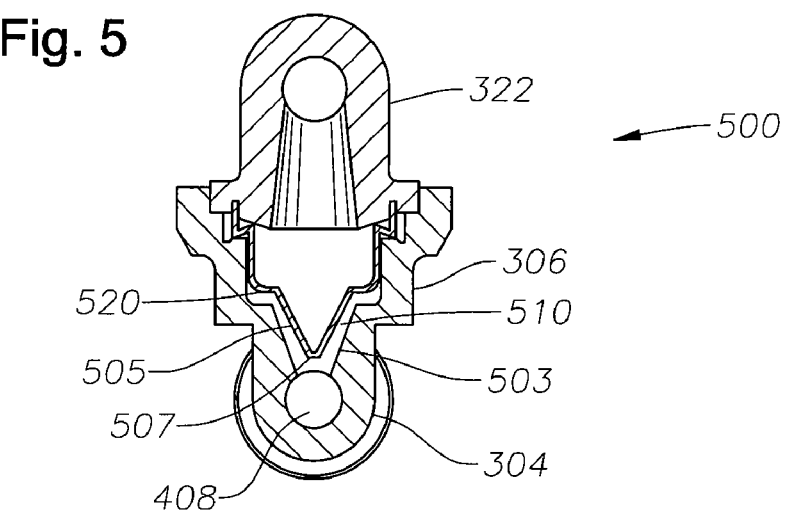
FIG. 5 is sectional view of the automatic stop cock valve system of FIG. 4 along line A-A.

FIGS. 4-5 show a second, preferred embodiment 500 of the automatic stop cock valve 20 of the present invention enclosed within a tee-shaped fitting 502. Preferred embodiment 500 employs a stem portion 306 with a receptacle 501 for receiving a duck bill valve 520. Preferred embodiment 500 is substantially identical in structure and operation to preferred embodiment 300 with the exceptions that fitting 322 is ultrasonically bonded to stem portion 306, duck bill valve 520 is rotated ninety degrees within fitting 502 as compared to the disposition of duckbill valve 320 within fitting 302, and the geometries of receptacle 501 and duckbill valve 520 have been slightly modified. More specifically, by rotating duck bill valve 520 by ninety degrees, unwanted turbulence and the associated air or gas bubbles within the infusion solution flow within portion 304 are prevented. Similar to preferred embodiment 300, receptacle 501 has an internal surface 503 closely mating with an external surface 505 of valve 520. In addition, a tip or opening surface 507 of valve 520 is disposed as close as possible to lumen 408 of straight portion 304 without placing valve 520 within the stream of fluid flow. Such a geometry of receptacle 501 and disposition of valve 520 minimizes or eliminates the gap volume 510 between receptacle 501 and external surface 505, which in turn prevents the formation of air or gas bubbles within the infusion solution flow within portion 304. Prevention of such air or gas bubbles maximizes patient safety.

While the present invention has been shown and described according to its preferred and alternate embodiments, those of ordinary skill in the art will understand that still other embodiments have been enabled by the foregoing disclosure. Such other embodiments shall be included within the scope and meaning of the appended claims.

What is claimed is:

1. A flow control system, comprising:
   a source for the flow of a first fluid;
   a source for the flow of a second fluid;
   means for switching between said flow of said first fluid and said flow of said second fluid;
   a first line for said flow of said first fluid;
   a second line for said flow of said second fluid; and
   a fitting comprising:
      a first entry portal for said first line;
      a second entry portal for said second line;
      an exit portal for either said first fluid or said second fluid;
      a normally closed duck bill valve, said duck bill valve having first and second bill portions capable of being opened when said means for switching between said flow of said first fluid and said flow of said second fluid switches said flow of said first fluid to said flow of said second fluid; and
      a receptacle having an internal surface closely mating with an external surface of said duck bill valve so as to minimize a gap volume between said receptacle and said external surface, dispose a tip of said first and second bill portions proximate said first flow of fluid, and dispose said first and second bill portions parallel to said flow of said first fluid.

2. The flow control system of claim 1 wherein:
said first line is an infusion line for a flow of liquid; and
said second line is a gas line for a flow of gas.

3. The flow control system of claim 2 whereby said disposing of said first and second bill portions parallel to said flow of said first fluid prevents turbulence and gas bubbles within said flow of said first fluid.

* * * * *